US00PP23088P2

(12) United States Plant Patent

Klemm et al.

(10) Patent No.: US PP23,088 P2

(45) Date of Patent: Sep. 25, 2012

(54) *NEMESIA* PLANT NAMED 'KLENH10726'

(50) Latin Name: *Nemesia hybrida*
Varietal Denomination: KLENH10726

(75) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/065,822

(22) Filed: Mar. 29, 2011

(51) Int. Cl.
*A01H 5/00* (2006.01)

(52) U.S. Cl. ..... Plt./458

(58) Field of Classification Search ..... Plt./458
See application file for complete search history.

*Primary Examiner* — Kent L Bell

(74) *Attorney, Agent, or Firm* — Jondle & Associates, P.C.

(57) ABSTRACT

A new variety of *Nemesia* named 'KLENH10726' particularly characterized by large, violet-colored flowers, good flower performance, and good branching, is disclosed.

1 Drawing Sheet

Genus and species: *Nemesia hybrida.*
Variety denomination: 'KLENH10726'.

BACKGROUND OF THE NEW PLANT

The present invention comprises a new and distinct variety of *Nemesia*, botanically known as *Nemesia hybrida*, and hereinafter referred to by the variety name 'KLENH10726'. This new *Nemesia* variety was discovered in June 2005 in Stuttgart, Germany and originated from an open pollination between the proprietary female parent 'SB1' and an unknown male parent. A single plant selection was subsequently chosen for further evaluation and asexual propagation.

The new variety was first propagated via vegetative cuttings and in-vitro propagation in May 2006 in Stuttgart, Germany and has been asexually reproduced repeatedly by vegetative cuttings in Stuttgart, Germany for over five generations. 'KLENH10726' has been found to retain its distinctive characteristics through successive asexual propagations.

Plant Breeder's Rights for this variety were applied for in Canada on Mar. 30, 2010. 'KLENH10726' has not been made publicly available more than one year prior to filing of this application.

SUMMARY OF THE INVENTION

The following are the most outstanding and distinguishing characteristics of this new variety when grown under normal horticultural practices in a greenhouse in hanging baskets.

1. Large, violet-colored flowers;
2. Good flower performance; and
3. Good branching.

DESCRIPTION OF THE PHOTOGRAPH

This new *Nemesia* plant is illustrated by the accompanying photograph which shows inflorescences and foliage of the plant. The colors shown are as true as can be reasonably obtained by conventional photographic procedures. The photograph was taken in Summer 2010 of a plant about 27 weeks old and grown from rooted cuttings in 15 centimeter pots in a greenhouse in hanging baskets under normal horticultural practices.

DESCRIPTION OF THE NEW VARIETY

The following detailed descriptions set forth the distinctive characteristics of 'KLENH10726'. The data which define these characteristics were collected from asexual reproductions carried out in Stuttgart, Germany. The plant history was taken in the Summer of 2010 on 27-week old plants in 15 centimeter pots in a greenhouse in hanging baskets. The plants were pinched once at 10 weeks. The color readings were determined under natural light. Color references are primarily to The R.H.S. Colour Chart of The Royal Horticultural Society of London (R.H.S.), Fifth Edition (2007).

DESCRIPTION OF THE NEW PLANT

Classification:
- *Family.*—Scrophulariaceae.
- *Genus and species.—Nemesia hybrida.*
- *Common name.—Nemesia.*

Parentage:
- *Female parent.*—The proprietary female *Nemesia* plant 'SB1'.
- *Male parent.*—The proprietary male plant is unknown due to an open pollination.

Plant:
- *Habit or form.*—Upright.
- *Vigor.*—Medium.
- *Height (measured from the top of the soil, including any flowers).*—43.0 cm.
- *Spread/width (horizontal plant diameter, including any flowers).*—52.0 cm.
- *Life cycle.*—Annual.
- *Time to produce a rooted cutting.*—4 weeks.
- *Time to produce a finished flowering plant.*—6 weeks after potting.
- *Flowering season.*—Spring.
- *Root description.*—White, fleshy.

Branches:
*Type*.—Basal.
*Quantity per plant*.—20.
*Length*.—33.0 cm.
*Diameter*.—0.5 cm.
*Internode length*.—2.3 cm.
*Strength of branches*.—Strong.
*Color*.—RHS 143C.
*Texture*.—Smooth.
*Stem anthocyanin*.—Absent.
*Branch pubescence*.—Absent.

Leaves:
*Arrangement*.—Opposite.
*Shape*.—Oval.
*Apex*.—Obtuse.
*Base*.—Obtuse.
*Margin*.—Serrate.
*Length*.—3.2 cm.
*Width*.—1.3 cm.
*Color*.—Upper surface: RHS 147A. Lower surface: RHS 147C.
*Variegation*.—Absent.
*Fragrance*.—Absent.
*Surface texture* (*both surfaces*).—Smooth.
*Pubescence*.—Absent.
*Venation pattern*.—Pinnate at first impression, parallel.
*Venation color*.—Upper surface: RHS 147A. Lower surface: RHS 147C.
*Petioles*.—Length: 0.3 cm. Diameter: 0.2 cm. Color: RHS 147A fading RHS 145B. Texture: Smooth.

Flower bud:
*Quantity per inflorescence*.—3.
*Shape*.—Oval.
*Surface texture*.—Smooth.
*Length*.—0.6 cm.
*Diameter*.—0.4 cm.
*Color*.—RHS 77A with RHS 158B segments depending on bud stage.

Inflorescence:
*Quantity of flowers per inflorescence*.—4 to 6 flowering together, up to more than 25 as whole.
*Inflorescence length*.—10.0 cm.
*Inflorescence diameter*.—0.2 cm.
*Flower diameter*.—2.2 cm.
*Flower depth* (*including nectar spur*).—1.3 cm.
*Nectar spur length*.—0.4 cm.
*Fragrance*.—Present.
*Self-cleaning or persistent*.—Self-cleaning.
*Lastingness of inflorescence*.—3 weeks.

Petals:
*Quantity per flower*.—5.
*Length*.—Upper lip: 1.0 cm. Lower lip: 1.3 cm.
*Width*.—Upper lip: 2.2 cm. Lower lip: 1.7 cm.
*Arrangement and shape*.—Solitary, zygomorphic and bilabiate with nectar spur arranged racemes.
*Apex*.—Obtuse.
*Margin*.—Entire.
*Color* (*mature*).—Both upper lip and lower lip (both upper and lower surfaces): RHS 83A fading to RHS 83C.
*Nectar spur color*.—RHS 93C with RHS 158B segments.
*Nectar guide color*.—RHS 5B placed on a white ground RHS 155D with RHS 93C segments.
*Spur length*.—0.5 cm.
*Spur diameter at the base*.—0.3 cm.
*Spur diameter at the tip*.—0.1 cm.
*Spur texture*.—Smooth.

Calyx:
*Shape*.—Star-shaped.
*Sepals*.—Quantity: 5. Shape: Sepal fused at base. Apex: Cuspidate. Base: Obtuse. Margin: Entire. Color: Upper surface: RHS 147A. Lower surface: RHS 147C. Length: 0.5 cm. Diameter: 0.2 cm. Surface texture (both surfaces): Hairy but smooth.

Pedicel:
*Length*.—1.8 cm.
*Diameter*.—0.1 cm.
*Color*.—RHS 146B.
*Surface texture*.—Hairy but smooth.

Peduncle:
*Length*.—3.4 cm.
*Diameter*.—0.2 cm.
*Color*.—RHS 146B.
*Surface texture*.—Smooth.

Reproductive organs:
*Stamens*.—Number per flower: 4 wrapped around pistil. Length: 0.3 cm. Filament color: RHS 157D. Filament length: 0.3 cm. Filament diameter: 0.05 cm. Anther color: RHS 7B. Anther length: 0.05 cm. Pollen amount: Moderate. Pollen color: RHS 7B.
*Pistil*.—Pistil number: 1. Pistil length: 0.1 cm. Stigma color: RHS 145D. Stigma length: 0.05 cm. Style length: 0.05 cm. Style color: RHS 145D.
*Ovary*.—Shape: Oval. Color: RHS 145B.

Fruit and seed set: None observed.
Disease and insect resistance: Normal.

COMPARISON WITH PARENTAL AND COMMERCIAL VARIETIES

'KLENH10726' differs from the proprietary female *Nemesia* plant 'SB1' in that 'KLENH10726' has violet flowers and good branching, while 'SB1' has purple-pink flowers and medium branching.

'KLENH10726' differs from the commercial cultivar 'KLENE04146' (U.S. Plant Pat. No. 18,360) in that 'KLENH10726' is a tall plant with large flowers, while 'KLENE04146' is a shorter plant with small flowers. In addition, 'KLENH10726' has a poor seed set, while 'KLENE04146' has a high seed set.

We claim:

1. A new and distinct variety of *Nemesia* plant named 'KLENH10726' as shown and described herein.

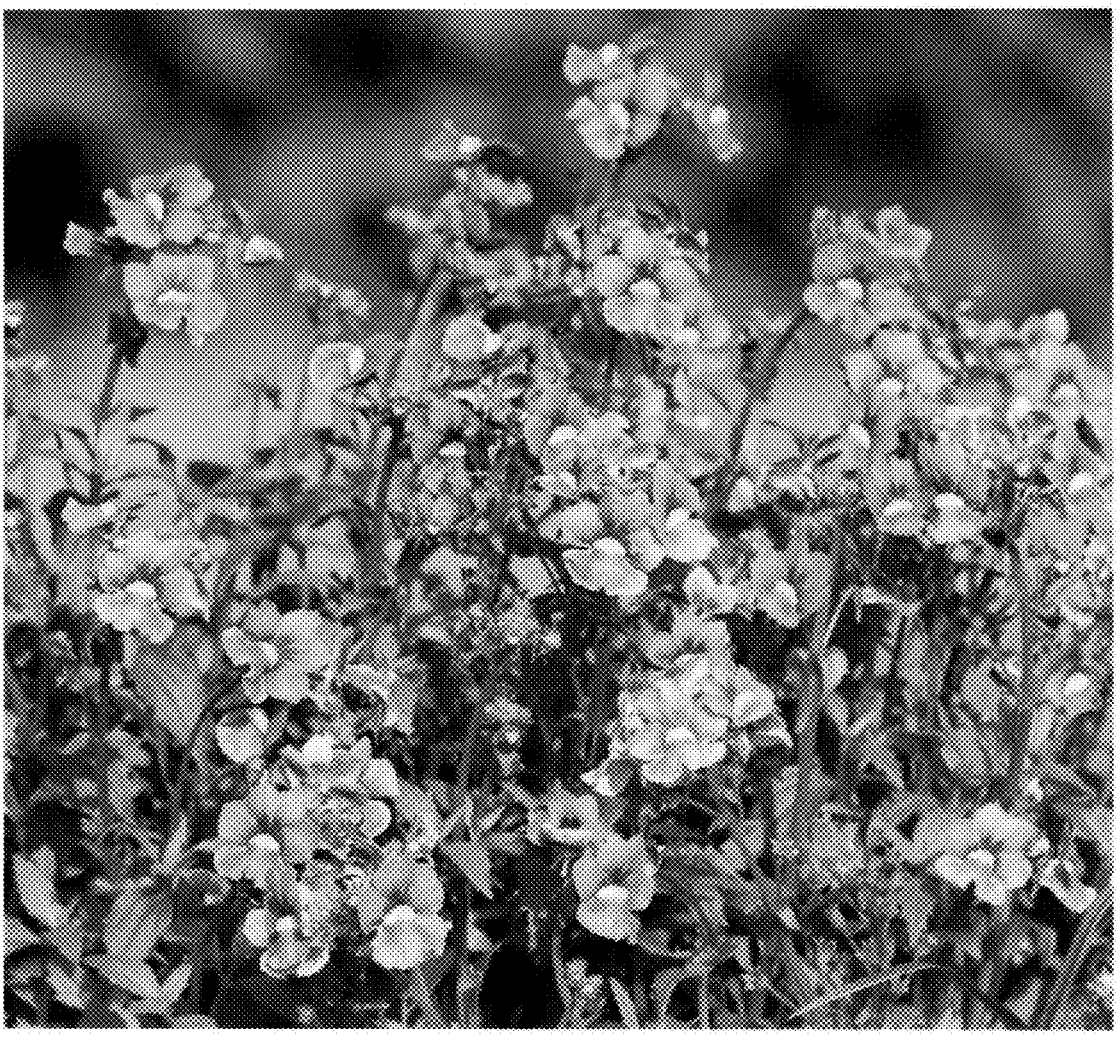

* * * * *